United States Patent [19]

Bodor et al.

[11] 4,069,322

[45] Jan. 17, 1978

[54] PRO-DRUGS FOR THE IMPROVED DELIVERY OF CERTAIN SELECTED ANTI-INFLAMMATORY STEROIDS

[75] Inventors: Nicolae S. Bodor, Lawrence; Kenneth B. Sloan, Eudora, both of Kans.

[73] Assignee: INTERx Research Corporation, Lawrence, Kans.

[21] Appl. No.: 731,373

[22] Filed: Oct. 12, 1976

[51] Int. Cl.² ............... A61K 31/58; C07J 17/00
[52] U.S. Cl. ............... 424/241; 260/239.5; 260/239.55 D
[58] Field of Search ............... 260/239.5, 239.55 D; 424/241

[56] References Cited

FOREIGN PATENT DOCUMENTS

| | | | |
|---|---|---|---|
| 973,927 | 11/1964 | United Kingdom | 260/239.5 |
| 959,377 | 6/1964 | United Kingdom | 260/239.55 D |
| 996,079 | 6/1965 | United Kingdom | 260/239.55 D |
| 1,043,347 | 9/1966 | United Kingdom | 260/239.55 D |
| 1,199,362 | 7/1970 | United Kingdom | 260/239.55 D |

*Primary Examiner*—Elbert I. Roberts
*Attorney, Agent, or Firm*—Charles N. Blitzer

[57] ABSTRACT

Transient, pro-drug forms of conventional anti-inflammatory steroids are disclosed.

37 Claims, No Drawings

PRO-DRUGS FOR THE IMPROVED DELIVERY OF CERTAIN SELECTED ANTI-INFLAMMATORY STEROIDS

BACKGROUND OF THE INVENTION

1. FIELD OF THE INVENTION

The present invention is directed to certain selected transient pro-drug forms of conventional anti-inflammatory steroids (e.g., cortisone, hydrocortisone, prednisone, prednisolone, etc.) useful in alleviating inflammatory conditions in warm-blooded animals.

For the purposes of this application, the term "pro-drug" denotes a derivative of a known and proven prior art anti-inflammatory steroid compound (e.g., cortisone, hydrocortisone, prednisone, prednisolone, etc.), which derivative, when administered to a warm-blooded animal, "cleaves" in such a manner as to release the proven drug form at its target site or sites of activity.

The term "transient" denotes enzymatic and/or chemical hydrolytic "cleavage" of the compounds of the instant invention in such a manner such that the proven drug form (the conventional antiinflammatory steroid, e.g., cortisone, hydrocortisone, prednisone, prednisolone, etc.) is released while the remaining "cleaved" moiety remains nontoxic and is metabolized in such a manner that nontoxic, metabolic products are produced.

Finally, the term "pharmaceutically acceptable acid addition salt" as used herein generally includes the nontoxic acid addition salts of selected compounds of formulas (I) and (II), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, sulfonic, toluenesulfonic, and the like.

2. BACKGROUND OF THE INVENTION

Conventional anti-inflammatory steroids such as cortisone, hydrocortisone, prednisone, prednisolone, etc. are large molecular weight steroidal compounds containing a number of hydrophilic functions, e.g., hydroxyl and keto functions. These compounds are characterized as having (1) extremely low water solubility, (2) extensive intermolecular hydrogen bonding due to the combination of hydrophilic functions such as —OH and =O (as evidenced by their high melting point, and (3) high molecular weight.

All three points enumerated above contribute to the inefficient and slow penetrability of these conventional steroidal compounds through biological barriers, among which the most important are (1) the skin and (2) the gastrointestinal wall.

It is recognized that in the case of the skin, the higher molecular weight anti-inflammatory steroids are absorbed primarily through the appendages and the hair follicles as opposed to the more efficient molecular interacellular absorption. See, M. Katz and B. J. Poulsen, Absorption of Drugs through the Skin, Handbook of Experimental Pharmacology, Vol. XXVII/I, Chapter 7, page 104, Springer Verlag, Berlin — Heidelberg — New York, 1971.

In view of the foregoing, it is apparent that a need exists for a class of novel anti-inflammatory steroidal compounds which will overcome the aforementioned inefficiencies such that penetration of the same through biological barriers will be enhanced.

SUMMARY OF THE INVENTION

It is one object of the present invention to provide pro-drug forms of convenional anti-inflammatory steroids which possess the capability of efficiently penetrating the biological barriers of warm-blooded animals, and especially, the skin and the gastrointestinal wall.

It is another object of the present invention to provide such pro-drug forms of conventional anti-inflammatory compounds which, following adminstration, will "Cleave" in such a manner as to enable the original parent steroidal moiety (e.g., cortisone, hydrocortisone, prednisone, prednisolone, etc.) to be released at its therapeutic site or sites of anti-inflammatory activity and to further permit the cleaved moiety(ies) unassociated with the parent steroidal moiety to be metabolized in a nontoxic fashion.

All the foregoing objects are achieved by topically or orally administrating to a warm-blooded animal afflicted with inflammation, a therapeutically effective anti-inflammatory amount of a compound having a formula:

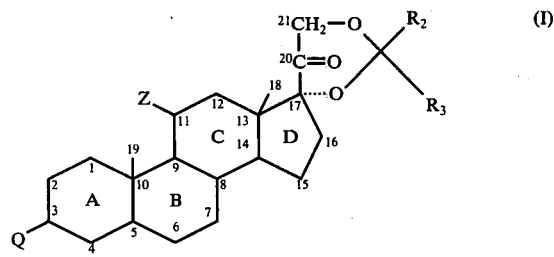

wherein Z represents a member selected from the group consisting of =O, β—OH and β—o—R$_1$, wherein R$_1$ represents

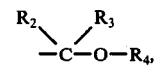

wherein R$_4$ represents a member selected from the group consisting of H and straight or branched C$_1$–C$_4$ alkyl, and wherein R$_2$ and R$_3$ which may be the same or different, represent a member selected from the group consisting of H, straight or branched C$_1$–C$_8$ alkyl, substituted C$_1$–C$_8$ alkyl, wherein at least one of the hydrogen atoms therein is substituted by a member selected from the group consisting of —N(R$_4$)$_2$, —CON(R$_4$)$_2$, a halogen atom (Cl, Br, I), —COOR$_4$, —COOCH$_2$N(R$_4$)$_2$ and —COOCH$_2$—S—R$_4$, wherein R$_4$ is defined as above, and wherein R$_2$ and R$_3$ further represent a member selected from the group consisting of

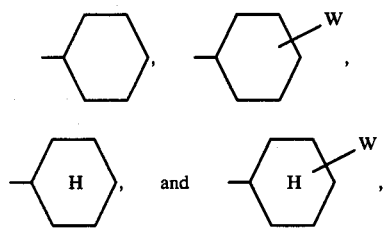

wherein W represents a member selected from the group consisting of —N(R$_4$)$_2$, —CON(R$_4$)$_2$, a halogen atom (Cl, Br, I), —COOR$_4$, —COOCH$_2$N(R$_4$)$_2$ and —COOCH$_2$—S—R$_4$, wherein R$_4$ is defined as above, with the proviso that R$_2$ and R$_3$ cannot simultaneously be H or wherein R$_2$ and R$_3$ taken together further represent a member selected from the group consisting of cyclic alkyl [-(CH$_2$)$_n$-] and cyclic heteroalkyl, wherein one of the carbon atoms is substituted by a member selected from the group consisting of <N-R$_4$, <N—COR$_4$ and —SO, wherein $n$ is an integer of 5 to 7 and wherein R$_4$ is defined as above; wherein Q represents a member selected from the group consisting of =O and

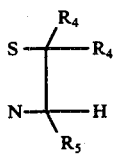

wherein R$_4$ is defined as above, and R$_5$ represents H, COOR$_4$ and —CON(R$_4$)$_2$, wherein R$_4$ is defined as above, provided that when Q is not =O, the C$_4$–C$_5$ double bond in formula (I) is subject to migration to the C$_5$–C$_6$ position; and wherein with respect to ring (A) in formula (I), the bond between C$_1$ and C$_2$ can be single or double bond.

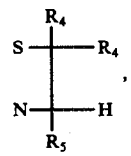 (II)

wherein Z represents a member selected from the group consisting of =O and β—OH; wherein R$_6$ represents a member selected from the group consisting of H and

with the proviso that one of said R$_6$ is H, wherein R$_7$ represents a member selected from the group consisting of a C$_1$–C$_{12}$ straight, branched or cycloalkyl, a C$_1$–C$_{12}$ straight, branched or cycloalkenyl, a substituted C$_1$–C$_{12}$ straight, branched or cycloalkyl or alkenyl,

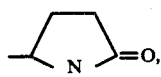

—(CH$_2$)$_n$—CON(R$_2$)$_2$, wherein $n$ is an integer of 1 to 6, a 2, 3 or 4 pyridyl, wherein at least one of the hydrogen atoms therein can be substituted by a member selected from the group consisting of —N(R$_4$)$_2$, —CON(R$_4$)$_2$, —SOR$_4$, a halogen atom (Cl, Br, I), —COOR$_4$, —COOCH$_2$N(R$_4$)$_2$ and —COOCH$_2$—S—R$_4$, wherein R$_4$ is defined above,

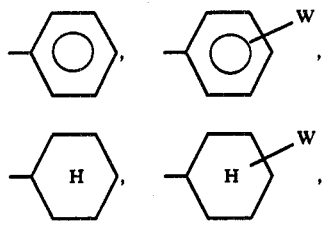

wherein W is defined above; wherein Q represents

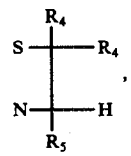

wherein R$_4$ is defined as above and R$_5$ represents a member selected from the group of consisting of H, COOR$_4$ and —CON(R$_4$)$_2$, wherein R$_4$ is defined as above; wherein the bond between C$_1$ and C$_2$ is ring "A" of formula (II) can be a single or a double bond; and wherein, with respect to ring "A" in formula (II), the double bond between C$_4$ and C$_5$ is subject to migration to the C$_5$—C$_6$ position, useful in treating inflammation in warm-blooded animals.

DETAILED DESCRIPTION OF THE INVENTION

With respect to generic formulas (I) and (II), reference to straight or branched "alkyl" and "alkenyl," denotes a preferred carbon range of from one (1) to five (5).

While all the compounds encompassed within the above-described generic formulas (I) and (II) essentially satisfy the objectives of the instant invention, nevertheless, certain selected compounds are set out below, remain preferred:

1 Spiro [Δ$^5$-pregnene-11β, 17α, 21-triol-20-one-3,2'-thiazolidine-4'-carboxylic acid]

2 Spiro [Δ$^5$-pregnene-21-acetyloxy-11β, 17α-diol-20-one-3,2'-thiazolidine-4'-carboxylic acid]

3. Spiro [Δ$^5$-pregnene-21-(N,N-dimethylglycyl)-oxy-11β, 17α-diol-20-one-3,2'-thiazolidine-4'-carboxylic acid]

4 Spiro [Δ$^5$-pregnene-11β,17α, 21-triol-20-one-3,2'-thiazolidine-4'-carboxylic acid ethyl ester]

5 Spiro [Δ$^5$-pregnene-21-acetyloxy-11β, 17α,-diol-20-one-3,2'-thiazolidine-4'-carboxylic acid ethyl ester]

6 Spiro [Δ$^5$-pregnen-21-(N,N-dimethylglycyl)-oxy-11β,17α-diol-20-one-3,2'-thiazolidine-4'-carboxylic acid ethyl ester]

7. Spiro [Δ$^5$-pregnene-17α, 21-diol-11, 20-dione-3,2'-thiazolidine-4'-carboxylic acid]

8. Spiro [Δ$^5$-pregnene-21-acetyloxy-17α-ol-11, 20-dione-3,2'-thiazolidine-4'-carboxylic acid]

9. Spiro [Δ$^5$-pregnene-21-(N,N-dimethylglycyl)-oxy-17αp-ol-11,20-dione-3, 2'-thiazlidine-4'-carboxylic acid]

10. Spiro [Δ$^5$-pregnene-17α,21-diol-11, 20-dione-3,2'-thiazolidine-4'-carboxylic acid ethyl ester]

11. Spiro [Δ$^5$-pregnene-21-acetyloxy-17α-ol-11, 20-dione-3, 2'-thiazlidine-4'-carboxylic acid ethyl ester]

12. Spiro [Δ⁵-pregnene-21-(N,N-dimethylglycyl)-oxy-17α-ol-11, 20-dione-3,2'-thiazolidine-4'-carboxylic acid ethyl ester]
13. Spiro [Δ¹,⁴-pregnadiene-11β, 17α, 21-triol-20-one-3, 2'-thiazolidine-4'-carboxylic acid]
14. Spiro [Δ¹,⁴-pregnadiene-21-acetyloxy-11β, 17α-diol-20-one-3, 2'-thiazolidine-4'-carboxylic acid]
15. Spiro [Δ¹,⁴-pregnadiene-21-(N,N-dimethylglycyl)-oxy-11β, 17α-diol-20-one-3, 2'-thiazolidine-4'-carboxylic acid]
16. Spiro [Δ¹,⁴-pregnadiene-11β,17α, 21-triol-20-one-3, 2'-thiazolidine-4'-carboxylic acid ethyl ester]
17. Spiro [Δ¹,⁴-pregnadiene-21-acetyloxy-11β,17α-diol-20-one-3, 2'-thiazolidine-4'-carboxylic acid ethyl ester]
18. Spiro [Δ¹,⁴-pregnadiene-21-(N,N-dimethylglycyl)-oxy-11β,17α-diol-20-one-3, 2'-thiazolidine-4'-carboxylic acid ethyl ester]
19. Spiro [Δ⁵-pregnene-17α, 21-isopropylidenedioxy-11β-ol-20-one-3, 2'-thiazlidine-4'-carboxylic acid]
20. Spiro [Δ⁵-pregnene-17α,21-isopropylidenedioxy-11β-ol-20-one-3,2'-thiazolidine-4'-carboxylic acid ethyl ester]
21. Spiro [Δ⁵-pregnene-17α, 21-(2-N,N-dimethylaminoethyl, methyl)-methylenedioxy-11β-ol-20-one-3, 2'-thizolidine-4'-carboxylic acid]
22. Spiro [Δ⁵-pregnene-17α, 21-(2-N,N-dimethylaminoethyl, methyl)-methylenedioxy-11β-ol-20-one-3, 2'-thiazolidine-4'-carboxylic acid ethyl ester]
23. Δ⁵-Pregnene-17α, 21-(2-N,N-dimethylamino-ethyl, methyl)-methylenedioxy-11β-ol-20-one
24. Δ⁵-Pregnene-17α17α-[4-(N,N-dimethylamino)methyl]-benzylidenedioxy-11β-ol-20-one
25. Δ⁵-Pregnene-17α,21-[(2-N,N-dimetylamido)ethyl, methyl]-methylenedioxy-11β-ol-20-one From among the foregoing listed "preferred" compounds, a select group of compounds remain "most preferred." These compounds are claimed hereinafter.

The compounds of the instant invention are easily prepared in accordance with those step-wise procedures outlined below. For convenience sake, "hydrocortisone" will be employed as a model conventional anti-inflammatory steroid moiety in the reaction schemes which follow. All amounts of reactants required (save for the steroid per se) are used in excess unless otherwise indicated.

SYNTHESIS FOR THE COMPOUNDS OF FORMULA (I) - WHEN Q IS OTHER THAN =O

In the first step, hydrocortisone is reacted with a compound having the formula:

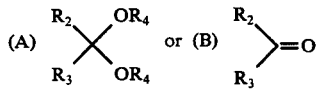

wherein $R_2$, $R_3$ and $R_4$ are defined above. Examples for this type of reactions are well known and were discussed in literature. See, R. Gardi, R. Vitali, and A. Ercoli, *J. Org. Chem.*, 27, 668 (1962); M. Tanabe and B. Biglby, *J. Amer. Chem. Soc.*, 83, 756 (1961). The reaction is run in the presence of an inert organic solvent, e.g., dimethylformamide, benzene, toluene, xylene, etc., and in the further presence of an organic or inorganic acid catalyst (p-toluenesulfonic acid, sulfosalicylic acid, HCl, HClO₄, etc.) preferably at the boiling point of the solvent employed while removing the resulting water or R₄—OH formed. The reaction is generally run at standard pressure for a period of time ranging from approximately 15 minutes to 6 hours.

Alternatively, in this first step, the reagents can be employed as the solvents, per se, in the presence or absence of an organic or inorganic acid catalyst such as p-toluenesulfonic acid, sulfosalicyclic acid, a sulfonic acid polymer, HCl, HClO₄, or alternatively, in the presence of a water scavenger such as CaC₂, a molecular sieve of from one to two A, etc. This alternative procedure is normally run at standard pressure, from room temperature to the boiling point of the solvent employed and for a period of time approximating one to 24 hours.

Next, the intermediate product of step (1) described above which can be generally referred to as a steroidal cyclic 1,3-dioxane-5-one which contains at the $C_{11}$ position at Z (heretofore defined), a β-OH moiety or the corresponding β-OR₁ moiety, wherein R₁ is defined above is obtained. This product thus obtained is next subjected to further transformation which essentially consists of exchanging the $C_3$ oxo group for a corresponding thiazolidine derivative (the "Q" moiety) by reacting such product with a reagent having the formula:

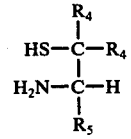

in the presence of a suitable organic solvent (e.g., benzene, toluene, xylene, dimetylformamide, etc.) and further in the presence of a suitable organic base (e.g., trimethylamine, triethylamine, pyridine, etc.). This reaction is carried out at standard pressure, a temperature of from room temperature to the boiling point of the solvent employed and for a period of time ranging from approximately 2 to 48 hours.

Spiro-thiazolidines from cysteine and various aldehydes have been previously described. See, H. Scubert, *J. Biol. Chem.*, 111, 671 (1935); 114, 341 (1936); 121, 539 (1937); 130, 601 (1939), and the approach was extended to 3-keto-steroids. See S. Lieberman, P. Brazeau and L. B. Hariton, *J. Amer. Chem. Soc.*, 70, 3094 (1948) and C. Djerassi and N. Crossley, *J. Amer. Chem. Soc.*, 84, 1112 (1962). It is, however, important to note that similar derivatives of Δ⁴-3-keto-steroids which are the objectives of this present invention, have not been synthesized, and more than this, attempts to synthesize them have completely failed. " . . . An unexpected finding was the failure of the α,β-unsaturated 3-keto-steroids to react with cysteine or its ethyl ester. Testosterone, . . . desoxycorticosterone, progesterone . . . did not form thiazolidines." (See, Lieberman, above ref., page 3096).

SYNTHESIS OF THE COMPOUND OF THE FORMULA (I) — WHEN Q REPRESENTS =O

In the first step, hydrocortisone is reacted with a compound of the formula:

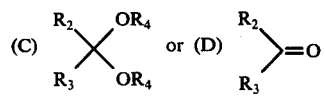

wherein $R_2$, $R_3$ and $R_4$ are defined as above. The reaction is run in the presence of an inert organic solvent (e.g., dimethylformamide, benzene, toluene, xylene, etc.) in the further presence of a suitable organic or inorganic acid catalyst (e.g., p-toluenesulfonic acid, sulfosalicyclic acid, HCl, $HClO_4$, etc.), preferably at the boiling point of the solvent employed while removing the resulting water or $R_4OH$ formed. The reaction is generally run at standard pressure and over a period of time ranging from 15 minutes to six hours.

Alternatively, in this reaction, the reagents themselves can be employed as the solvents per se in the presence or absence of an organic or inorganic acid catalyst (e.g., p-toluenesulfonic acid, a sulfonic acid polymer, HCl, $HClO_4$, etc.), or alternatively, in the presence of a water scavenger such as $CaC_2$, a molecular sieve of from one to two A, etc. The reaction is run at standard pressure, a temperature ranging from room temperature to the boiling point of the solvent employed and over a period of time approximating one to 24 hours.

The product obtained from the above-described reaction is the final product which is generally referred to a steroidal cyclic 1,3-dioxane-5-one, containing at the $C_{11}$ position, as Z, a $\beta$-OH moiety or the corresponding $\beta$-$OR_1$ moiety, wherein Z and $R_1$ are defined above.

SYNTHESIS OF THE COMPOUNDS OF FORMULA (II) — WHERE $R_6$ IS OTHER THAN HYDROGEN

Firstly, hydrocortisone is reacted with a conventional acylating agent of the formula:

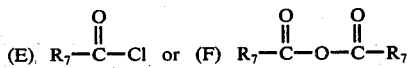

or $R_7$—COOH in the presence of a coupling agent such as DCCl, wherein $R_7$ is defined as above, thus obtaining the $C_{21}$ and/or $C_{17}$ acylate intermediate. This reaction is carried out at standard pressure, a temperature of from room temperature to the boiling point of the solvent employed, over a reaction time of from approximately one to 24 hours and in the presence of a suitable organic solvent (e.g., pyridine, benzene, toluene, xylene, dichloromethane, chloroform, acetic, propionic, butyric or other $R_7$ acids, etc.), in the presence or absence of an acid catalyst, such as p-toluenesulfonic or sulfosalycilic acid.

Next, the intermediate product obtained from the reaction described above is then subjected to the introduction of the "Q" moiety, the procedure for which is identical to that described for the second step of the preparatory procedure for synthesizing the compounds of formula (I), where Q is other than =O.

If need be, the final product can be recrystallized from a suitable organic solvent in the absence of oxygen, acidic compounds, ketones or aldehydes.

SYNTHESIS FOR THE COMPOUNDS OF FORMULA (II) — WHEN $R_6$ EQUALS H

This is a one-step procedure wherein the starting material (for example, hydrocortisone) is simply subjected to the second step of the preparatory procedure for synthesizing the compounds of formula (I) where Q is other than =O. If need be, the final product obtained can be recrystallized from a suitable organic solvent in the absence of oxygen, acidic compounds, ketones or aldehydes.

Without further elaboration, it is believed that one of ordinary skill in the art can, using the preceding description, utilize the instant invention to its utmost extent. The following preferred specific embodiments are, therefore, to be simply construed as merely illustrative and not limitative of the remainder of the specification and claims in any way whatsoever. All references to "temperature" in the following examples denote Centigrade unless otherwise indicated.

EXAMPLE I

The Preparation of
3-Spiro-(2'-Thiazolidine-4'-Carboethoxy)-11$\beta$, 17$\alpha$-Dihydroxy-21-Acetoxy-$\Delta$5, 6-Pregnene-20-One (I)

Hydrocortisone 21-acetate (8.1 g, 0.02 mole) was dissolved in pyridine (70 ml) and nitrogen was bubbled through the solution for 20 min. Cysteine ethyl ester hydrochloride (22.28 g, 0.12 mole) was then added to the solution which was kept at room temperature over night under a nitrogen atmosphere. The pyridine was distilled at 38° and the resulting residue was titrated with water and filtered. The residue was dissolved in dichloromethane and the dichloromethane solution was dried over sodium sulfate and concentrated to 300 ml. Heptane (100 ml) was added to the dichloromethane solution and the mixture was concentrated to 220 ml under a nitrogen atmosphere. The crystals obtained by cooling the solution to room temperature were filtered to give 5.52 g (mp 175°-176°, 52% yield) of I; a second crop of crystalline I was obtained upon refrigeration of the mother liquors (2.49 g, mp 161°-163°, 23% yield). The crystalline I was one spot upon analyses by TLC (silica gel, tetrahydrofuran-ether, 1.4, Rf 0.56): ir (KBr) 1710 and 1735 cm$^{-1}$(s)(C=O) and 3560, 3410 and 3275 cm$^{-1}$ (m) (N—H and OH); NMR (CDCl$_3$) $\delta$ 5.4 – 5.2 (m, 1, C=C—H), 5.0 – 4.8 (m, 2 $CH_2$—$_{OC=O}$), 4.6 – 3.9 (m, 4, $CH_2$—O, O=CCH—N and $CH_2$—O), 2.3 (s, 3, $CH_3C$=O), 1.47 (s, 3, $CH_3$—C) and 0.9 (s, 3, $CH_3$—C); $[\alpha]_b^{28}$ = +97.2 c=0.5 (ethanol).

Anal. Calcd for $C_{28}H_{40}NO_7S$: C, 62.78; H, 7.72; N, 2.62. Found: C, 62.63; H, 7.70; N, 2.30.

EXAMPLE II

The Preparation Of Hydrocortisone 17$\alpha$, 21-Acetonide (II)

A modification of the procedure of R. Gardi, et al [R. Gardi, R. Vitali and A. Ercoli, *J. Org. Chem.*, 27, 668 (1962)] was employed. Hydrocortisone (12 g, 0.033 mole) was suspended in 1500 ml of boiling benzene and 100 ml of benzene was distilled. Then 16 ml of dimethoxypropane was added to the benzene suspension followed immediately by 6 ml of a hot 0.4% p-toluene sulfonic acid in benzene solution. Benzene was distilled at a rapid rate from the resulting suspension and after 15 minutes a solution was obtained; the distillation was continued for 10 minutes after solution was obtained. Pyridine (0.5 ml) was added to quench the reaction which was cooled to room temperature. The benzene was evaporated in vacuo and the residue was adsorbed on silica gel cc-7 and chromatographed on silica gel cc-7 (600 g) using ether-heptane 1:9, 2:8 and ether-acetone-heptane 2:1:7 as the eluents in the above order to give the following fractions:

Fraction A. Part of fraction A crystallized while it was being collected. Those crystals were filtered to give 0.26 g (mp 173°–177°) of fine white needles designated fraction A(1) which was one spot upon analysis by TLC (silica gel, ether, Rf 0.44);ir (KBr) 3440 cm⁻¹ (s) (OH) 1710 and 1605 cm⁻¹ (w) and 1645 cm⁻¹ (s) (C=O); NMR (CDCl₃) δ 5.66 (s, 1, O=C—CH=CH), 5.33 (s, 1,

), 4.5–4.3 (m, 1, CH—OH), 3.4 (s, 3, O—CH₃), 1.53, 1.5 and 1.47 (s, 9, CH₃—C and

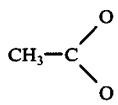

), 1.17 (s, 3, CH₃—C); $[\alpha]_D^{26}$ +150 c=0.59 (methanol); $\lambda_{max}^{methanol}$ 242 mμ (ε = 15,900); mass spectrum m/e 416 (m+).

Anal. Calcd for C₂₅H₃₆O₅: C, 72.08; H, 8.71. Found: C, 71.93; H, 8.79.

The mother liquor from fraction A(1) was concentrated in vacuo to give a white solid which was crystallized from ether-hexane to give 1.88 g (mp 164°–168°) of white crystals designated fraction A(2) which also was one spot upon analysis by TLC (silica gel, ether). Fraction A(2) was identical with A(1) in its mass spectrum fragmentation pattern, infrared spectrum, uv spectrum, TLC and exhibited the same elemental analysis as A(1). However, there was a distinct difference in the optical rotation of fraction A(2); $[\alpha]_D^{26}$ +123° c=0.55 (methanol). There were also differences in certain aspects of the NMR spectrum; the OCH₃ absorption and the CH₃—C absorption at 1.17 were split into approximately equal absorptions.

Fraction B. Fraction B was concentrated in vacuo and the residue was crystallized from heptane to give 323 mg (mp 144°–146°) of a white fibrous solid which was one spot upon analysis by TLC (silica gel, ether, Rf 0.36): ir (KBr) 3400 cm⁻¹(s) (OH), 1710 and 1605 cm⁻¹ (w) and 1645 cm⁻¹(s) (C=O); NMR (CDCl₃) δ 5.63 (s, 1, O=C—CH=C), 5.5–5.35 (m, 1, C=CH), 4.5–4.3 (m, 1, CH—OH), 3.37 (s, 3, O—CH₃), 1.50, 1.43 and 1.40 (three s, 9, CH₃—C) and 1.13 (s, 3, CH₃—C); $\lambda_{max}^{methanol}$ 242 mμ ε=16,600; $[\alpha]_D^{26}$ +163° c=0.45 (methanol); mass spectrum m/e 416.

Anal. Calcd for C₂₅H₃₆O₅: C, 72.08; H, 8.71. Found: C, 72.19; H, 8.87.

Fraction C. Part of fraction C crystallized while it was being collected. The crystals were filtered to give 3.71 g (mp 184°–185°) of fine white needles of the acetonide II. The mother liquor was slowly concentrated in steps to give more II: 0.79 g, mp 181°–182°; 0.75 g, mp 177°–179°, and finally 0.57 g, mp 176°–178°. The total yield of II which was one spot upon analysis by TLC (silica gel, ether, Rf 0.28) was 44%: ir (KBr) 3460 cm⁻¹ (s) (OH), 1700 and 1600 cm⁻¹ (m), and 1645 cm⁻¹ (s) (C=O); NMR (CDCl₃) δ 5.67 (s, 1, O=C—CH=), 4.5–4.3 (m, 1, CH—OH), 4.3–4.15 (m, 2, CH₂—OC=O), 1.47 (s, 9,

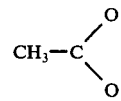

and CH₃—C) and 0.93 (s, 3, CH₃—C); $\lambda_{max}^{methanol}$ 242 mμ =16,300; $[\alpha]_D^{26}$ + 147° c=0.62 (methanol), mass spectrum m/e 402.

Anal. Calcd for C₂₄H₃₄O₅: C, 71.61; H, 8.51. Found: C, 71.42; H, 8.37.

EXAMPLE III

Preparation of 21(N,N-Dimethylglycyl)Hydrocortisone (III)

Pyridine (10 ml) was added to a mixture of 3.62 g (0.01 mole) of hydrocortisone, 2.26 g (0.011 mole) of dicyclohexylcarbodiimide and 1.54 g (0.011 mole) of dimethylglycine hydrochloride. The resulting well-stirred solution became solid within a few minutes. The solid was suspended in 100 ml of dichloromethane and the suspension was stirred overnight at room temperature. The suspension was filtered and the residue was resuspended in 300 ml of boiling chloroform. The chloroform suspension was filtered while still hot to give 4.05 g (mp 217°–220° (d), 83% yield) of III hydrate as a white nonhygroscopic solid: ir (KBr) 3400 cm⁻¹ (s) (O—H), 2800–2400 cm⁻¹ (w) (N+—H) and 1750, 1710, 1660 and 1610 cm⁻¹(s) (C=O); NMR (dmso—d₆) δ 5.5 (broad s, 2, one exchangeable proton and O=•C—CH=C), 5.3–4.95 (m, 2, CH₂—O—C=O), 4.33 (broad s, 3, CH—OH and CH₂—N+—H), 2.87 (s, 6, CH₃N+—H), 1.37 (s, 3, CH₃—C) and 0.77 (s, 3, CH₃—C).

Anal. Calcd for C₂₅H₄₀ClNO₇: C, 59.81; H, 8.03; N, 2.79. Found: C, 60.02; H, 7.72; N, 2.51.

EXAMPLE IV

Preparation of 3-Spiro (2:-Thiazolidine-4-Carboethoxy)-11β, 17α-Dihydroxy-21(N,N-Dimethylglycyl)-Δ5,6-Pregnene-20-One (IV)

A mixture of 2.0 g (0.0041 mole) of 21(N,N-dimethylglycyl)hydrocortisone and 4.60 g (0.025 mole) of cysteine ethyl ester hydrochloride in 12.5 ml of pyridine was stirred at room temperature overnight. The pyridine was distilled at 40° to give a foam. The foam was dissolved in water and IV was precipitated by making the solution basic with 5% sodium bicarbonate. The precipitate was filtered and dissolved in chloroform. The chloroform solution was dried over sodium sulfate and the chloroform was evaporated in vacuo to give 2.2 g of IV as a tan foam: mp 104°–108°, ir (KBr) 3400 cm⁻¹(m) (OH), 2800–2400 cm⁻¹ (s) (N+H), 1750 cm⁻¹ (s) (C=O) and 1630 and 1600 cm⁻¹(m); NMR (CDCl₃) δ 5.0 (m, 2, CH₂—OC=O), 4.6–4.0 (m, 4, CH₂—O, CH—OH and O=C—CH—N), 3.33 (s, 2, O=CCH-₂—N), 2.4 (s, 6, CH₃—N), 1.3 (s, 3, CH₃—C) and 0.93 (s, 3, CH₃—C).

In similar fashion, the remaining compounds of the present invention can be prepared with similar success by merely following the preceding examples and substituting the appropriate generically and/or specifically described reactants and/or operating conditions of this invention for those of the preceding examples. Thus, the following additional compounds can be prepared by following the above reaction scheme:

COMPOUNDS OF FORMULA I

| Example Number | Q | Z | $R_2$ | $R_3$ | Δ |
|---|---|---|---|---|---|
| 5 | =O | OH | $N(CH_3)_2$ | $N(CH_3)_2$ | 4,5 |
| 6 | =O | OH | H | cyclohexyl–$N(CH_3)_2$ | 4,5 |
| 7 | =O | OH | $CH_3$ | $N(CH_3)_2$ | 4,5 |
| 8 | =O | OH | $-CH_2CH_2N(CH_3)CH_2CH_2-$ | | 4,5 |
| 9 | =O | OH | $-CH_2CH_2N(COCH_3)CH_2CH_2-$ | | 4,5 |
| 10 | =O | OH | $-CH_2CH_2SO-CH_2CH_2-$ | | 4,5 |
| 11 | =O | OH | $-CH_2CH_2N(COCH_3)CH_2CH_2-$ | | 5,6 |
| 12 | thiazolidine-$CO_2C_2H_5$ | OH | $CH_3$ | $CH_3$ | 5,6 |
| 13 | =O | O | $N(CH_3)_2$ | $N(CH_3)_2$ | 1,2 & 4,5 |
| 14 | =O | O | H | cyclohexyl–$N(CH_3)_2$ | 1,2 & 4,5 |
| 15 | =O | O | $CH_3$ | $N(CH_3)_2$ | 1,2 & 4,5 |
| 16 | =O | O | $-CH_2CH_2N(CH_3)CH_2CH_2-$ | | 1,2 & 4,5 |
| 17 | =O | O | $-CH_2CH_2N(COCH_3)CH_2CH_2-$ | | 1,2 & 4,5 |
| 18 | =O | O | $-CH_2CH_2SO-CH_2CH_2-$ | | 1,2 & 4,5 |
| 19 | =O | O | $-CH_2CH_2N(COCH_3)CH_2CH_2-$ | | 1,2 & 4,5 |
| 20 | thiazolidine-$CO_2C_2H_5$ | O | $CH_3$ | $CH_3$ | 1,2 & 4,5 |

COMPOUNDS OF FORMULA II

| Example Number | Q | Z | $R_6$ | $R_7$ | Δ |
|---|---|---|---|---|---|
| 21 | =O | OH | $-CO-N$(imidazolyl) | H | 4,5 |
| 22 | =O | OH | $COCH_2CH_2CON(CH_3)_2$ | H | 4,5 |
| 23 | =O | OH | $COCH_2CH_2CON(C_2H_5)_2$ | H | 4,5 |
| 24 | =O | OH | $COCH_3CH_2CON$(morpholinyl) | H | 4,5 |
| 25 | =O | OH | CO-(5-oxopyrrolidin-2-yl) | H | 4,5 |
| 26 | thiazolidine-$CO_2C_2H_5$ | OH | H | $COC_3H_7$ | 5,6 |
| 27 | thiazolidine-$CO_2C_2H_5$ | OH | $COCH_2CH_2CON(C_2H_5)_2$ | H | 5,6 |

-continued

COMPOUNDS OF FORMULA II

| Example Number | Q | Z | $R_6$ | $R_7$ | Δ |
|---|---|---|---|---|---|
| 28 | spiro thiazolidine with N-H, $CO_2C_2H_5$ | OH | CO-(2-oxopyrrolidin-5-yl) | H | 5,6 |
| 29 | =O | O | -CO-N(imidazolyl) | H | 1,2 & 4,5 |
| 30 | =O | O | $COCH_2CH_2CON(CH_3)_2$ | H | 1,2 & 4,5 |
| 31 | =O | O | $COCH_2CH_2CON(C_2H_5)_2$ | H | 1,2 & 4,5 |
| 32 | =O | O | $COCH_3CH_2CON$(morpholino) | H | 1,2 & 4,5 |
| 33 | =O | O | CO-(2-oxopyrrolidin-5-yl) | H | 1,2 & 4,5 |
| 34 | spiro thiazolidine with N-H, $CO_2C_2H_5$ | O | H | $COC_3H_7$ | 1,2 & 4,5 |
| 35 | spiro thiazolidine with N-H, $CO_2C_2H_5$ | O | $COCH_2CH_2CON(C_2H_5)_2$ | H | 1,2 & 4,5 |
| 36 | spiro thiazolidine with N-H, $CO_2C_2H_5$ | O | CO-(pyrrolidin-2-yl) | H | 1,2 & 4,5 |

The compounds of the present invention are conveniently administered to warm-blooded animals via conventional oral or topical administration with any suitable nontoxic pharmaceutically acceptable oral or topical inert carrier material. Such carrier materials are well-known to those skilled in the art of oral and topical pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, any one of the compounds of the instant invention is combined in an anti-inflammatory effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars, such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alaginic acid, guar gum, citris pulp, carboxymethylcellulose and sodium lauryl sulfate. If desired a conventionally pharmaceutically acceptable dye can be incorporated into the dosage unit form, i.e., any of the standard FD&C dyes.

Similarly, in a typical formulation for topical application, any one of the compounds of the instant invention is combined with triacetin, such that the active ingredient is present in an anti-inflammatory effective amount. The preparation is simply applied topically to the inflamed area, whereby the therapeutically active compound is dermally absorbed and "cleaved" to release the parent steroidal moiety at the site of inflammation.

Naturally, the therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional steroid moiety (e.g., cortisone, hydrocortisone, prednisone, prednisolone, etc.). On a topical basis, application of a 0.01% to 2.5% concentration of a compound of the instant invention (in a suitable topical carrier material) to the site of inflammation should suffice.

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of equivalence of the following claims.

What we claim is:

1. A pro-drug compound of the formula:

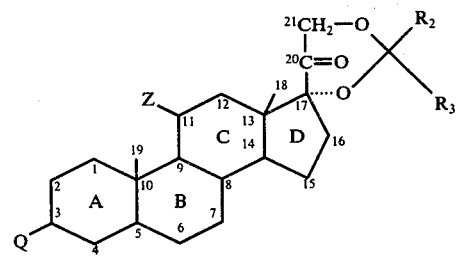

(I)

wherein Z represents a member selected from the group consisting of $=O$, $\beta$—OH and $\beta$—O—$R_1$, wherein $R_1$ represents

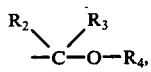

wherein $R_4$ represents a member selected from the group consisting of H and straight or branched $C_1$-$C_4$ alkyl, and wherein $R_2$ and $R_3$ which may be the same or different, represent a member selected from the group consisting of H, straight or branched $C_1$-$C_8$ alkyl, substituted $C_1$-$C_8$ alkyl, wherein at least one of the hydrogen atoms therein is substituted by a member selected from the group consisting of —N($R_4$)$_2$, —CON($R_4$)$_2$, a halogen atom, —COOR$_4$, —COOCH$_2$N($R_4$)$_2$ and —COOCH$_2$—S—$R_4$, wherein $R_4$ is defined as above, and wherein $R_2$ and $R_3$ further represent a member selected from the group consisting of

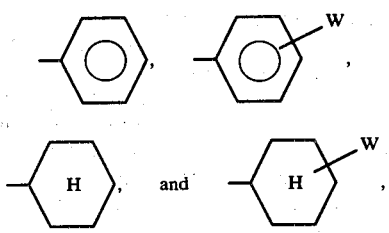

wherein W represents a member selected from the group consisting of —N($R_4$)$_2$, —CON($R_4$)$_2$, a halogen atom, —COOR$_4$, —COOCH$_2$N($R_4$)$_2$ and —COOCH$_2$—S—$R_4$, wherein $R_4$ is defined as above, with the proviso that $R_2$ and $R_3$ cannot simultaneously be H or wherein $R_2$ and $R_3$ taken together further represent a member selected from the group consisting of cyclic alkyl [-(CH$_2$)$_n$-] and cyclic heteroalkyl, wherein one of the carbon atoms is substituted by a member selected from the group consisting of <N—$R_4$, <N—COR$_4$ and —CO, wherein $n$ is an integer of 5 to 7 and wherein $R_4$ is defined as above; wherein Q represents

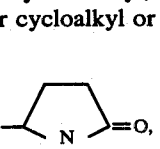

wherein $R_4$ is defined as above, and $R_5$ represents H, COOR$_4$ and —CON($R_4$)$_2$, wherein $R_4$ is defined as above, provided that the $C_4$-$C_5$ double bond in formula (I) is subject to migration to the $C_5$-$C_6$ position; and wherein with respect to ring (A) in formula (I), the bond between $C_1$ and $C_2$ can be a single or double bond:

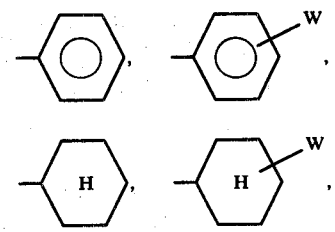

(II)

wherein Z represents a member selected from the group consisting of $=O$ and $\beta$—OH; wherein $R_6$ represents a member selected from the group consisting of H and $$-\overset{O}{\underset{\|}{C}}-R_7,$$

with the proviso that one of said $R_6$ is H, wherein $R_7$ represents a member selected from the group consisting of a $C_1$-$C_{12}$ straight, branched or cycloalkyl, a $C_1$-$C_{12}$ straight, branched or cycloalkenyl, a substituted $C_1$-$C_{12}$ straight, branched or cycloalkyl or alkenyl, —(CH$_2$)$_n$—CON($R_2$)$_2$, wherein $n$ is an integer of 1 to 6, a 2, 3 or 4 pyridyl, wherein at least one of the hydrogen atoms therein can be substituted by a member selected from the group consisting of —N($R_4$)$_2$, —CON($R_4$)$_2$, —SOR$_4$, a halogen atom, —COOR$_4$, —COOCH$_2$N($R_4$)$_2$ and —COOCH$_2$—S—$R_4$, wherein $R_4$ is defined above, wherein W is defined above; wherein Q represents

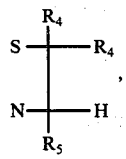

wherein $R_4$ is defined as above and $R_5$ represents a member selected from the group consisting of H, COOR$_4$ and —CON(R$_4$)$_2$, wherein R$_4$ is defined as above; wherein the bond between C$_1$ and C$_2$ in ring "A" of formula (II) can be a single or a double bond; and wherein, with respect to ring "A" in formula (II), the double bond between C$_4$ and C$_5$ is subject to migration to the C$_5$–C$_6$ position.

2. The compound of claim 1:
Spiro [Δ$^5$-pregnene-17α, 21-diol-11, 20-dione-3,2'-thiazolidine-4'-carboxylic acid]

3. The compound of claim 1:
Spiro [Δ$^5$-pregnene-21-acetyloxy-17α-ol-11, 20-dione-3,2'-thiazolidine-4'-carboxylic acid]

4. The compound of claim 1:
Spiro [Δ$^5$-pregnene-21-(N,N-dimethylglycyl)-oxy-17α-ol-11, 20-dione-3,2'-thiazolidine-4'-carboxylic acid]

5. The compound of claim 1:
Spiro [Δ$^5$-pregnene-17α, 21-diol-11, 20-dione-3,2'-thiazolidine-4'-carboxylic acid ethyl ester]

6. The compound of claim 1:
Spiro [Δ$^5$-pregnene-21-(N,N-dimethylglycyl)-oxy-17α-ol-11, 20-dione-3,2'-thiazolidine-4'-carboxylic acid ethyl ester]

7. The compound of claim 1:
Spiro [Δ$^{1,4}$-pregnadiene-11β, 17α, 21-triol-20-one-3, 2'-thiazolidine-4'-carboxylic acid]

8. The compound of claim 1:
Spiro [Δ$^{1,4}$-pregnadiene-21-acetyloxy-11β, 17αdiol-20-one-3,2'-thiazolidine-4'carboxylic acid]

9. The compound of claim 1:
Spiro [Δ$^{1,4}$-pregnadiene-21-(N,N-dimethylglycyl)-oxy-11β, 17α-diol-20-one-3,2'-thiazolidine-4'-carboxylic acid]

10. The compound of claim 1:
Spiro [Δ$^{1,4}$-pregnadiene-21-(N,N-dimethylglycyl)-oxy-11β, 17α-diol-20-one-3,2'-thiazolidine-4'carboxylic acid ethyl ester]

11. The compound of claim 1:
Spiro [Δ$^5$-pregnene-17α, 21-isopropylidenedioxy-11β-ol-20-one-3,2'-thiazolidine-4'-carboxylic acid]

12. A pharmaceutical composition of matter comprising an anti-inflammatory effective amount of a pro-drug compound of the formula:

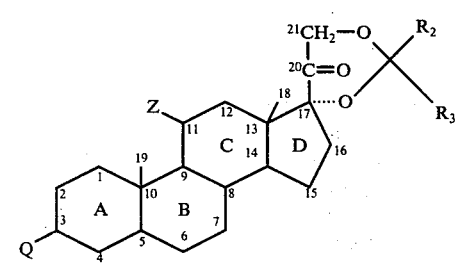

wherein Z represents a member selected from the group consisting of =O, β—OH and β—O—R$_1$, wherein R$_1$ represents

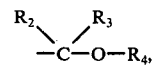

wherein R$_4$ represents a member selected from the group consisting of H and straight or branched C$_1$–C$_4$ alkyl, and wherein R$_2$ and R$_3$ which may be the same or different, represent a member selected from the group consisting of H, straight or branched C$_1$–C$_8$ alkyl, substituted C$_1$–C$_8$ alkyl, wherein at least one of the hydrogen atoms therein is substituted by a member selected from the group consisting of —N(R$_4$)$_2$, —CON(R$_4$)$_2$, a halogen atom, —COOR$_4$, —COOCH$_2$N(R$_4$)$_2$ and —COOCH$_2$—S—R$_4$, wherein R$_4$ is defined as above, and wherein R$_2$ and R$_3$ further represent a member selected from the group consisting of

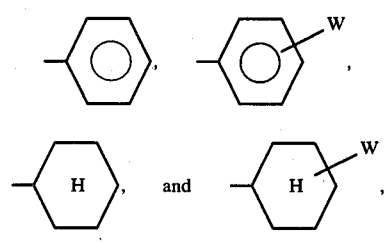

wherein W represents a member selected from the group consisting of —N(R$_4$)$_2$, —CON(R$_4$)$_2$, a halogen atom, —COOR$_4$, —COOCH$_2$N(R$_4$)$_2$ and —COOCH$_2$—S—R$_4$, wherein R$_4$ is defined as above, with the proviso that R$_2$ and R$_3$ cannot simultaneously be H or wherein R$_2$ and R$_3$ taken together further represent a member selected from the group consisting of cyclic alkyl [—(CH$_2$)$_n$—] and cyclic heteroalkyl, wherein one of the carbon atoms is substituted by a member selected from the group consisting of <N—R$_4$, <—COR$_4$ and <—CO, wherein n is an integer of 5 to 7 and wherein R$_4$ is defined as above; wherein Q represents

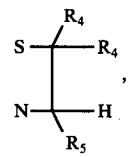

wherein R$_4$ is defined as above, and R$_5$ represents H, COOR$_4$ and —CON(R$_4$)$_2$, wherein R$_4$ is defined as above, provided that the C$_4$–C$_5$ double bond in formula (I) is subject to migration to the C$_5$–C$_6$ position; and wherein with respect to ring (A) in formula (I), the bond between C$_1$ and C$_2$ can be a single or double bond.

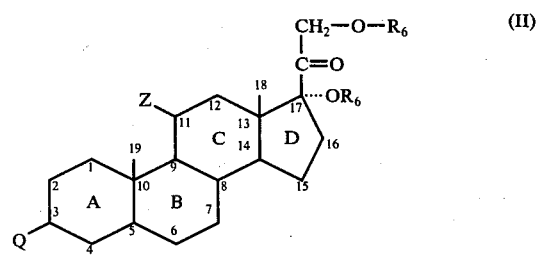

wherein Z represents a member selected from the group consisting of =O and β—OH; wherein R₆ represents a member selected from the group consisting of H and

with the proviso that one of said R₆ is H, wherein R₇ represents a member selected from the group consisting of a $C_1$-$C_{12}$ straight, branched or cycloalkyl, a $C_1$-$C_{12}$ straight, branched or cycloalkenyl, a substituted $C_1$-$C_{12}$ straight, branched or cycloalkyl or alkenyl,

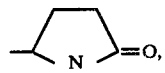

—(CH₂)ₙ—CON(R₂)₂, wherein n is an integer of 1 to 6, a 2, 3 or 4 pyridyl, wherein at least one of the hydrogen atoms therein can be substituted by a member selected from the group consisting of —N(R₄)₂, —CON(R₄)₂, —SOR₄, a halogen atom, —COOR₄, —COOCH₂N(R₄)₂ and —COOCH₂—S—R₄, wherein R₄ is defined above,

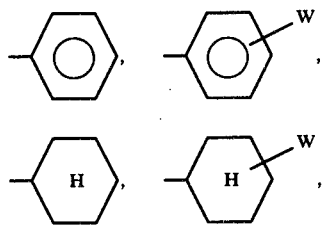

wherein W is defined above; wherein Q represents

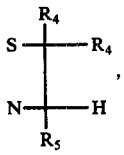

wherein R₄ is defined as above and R₅ represents a member selected from the group consisting of H, COOR₄ and —CON(R₄)₂, wherein R₄ is defined as above; wherein the bond between C₁ and C₂ in ring "A" of formula (II) can be a single or a double bond; and wherein, with respect to ring "A" in formula (II), the double bond between C₄ and C₅ is subject to migration to the C₅-C₆ position.

13. The composition of claim 12, wherein said compound is:
Spiro [Δ⁵-pregnene-17α, 21-diol-11, 20-dione-3,2'-thiazolidine-4'-carboxylic acid]

14. The composition of claim 12, wherein said compound is:
Spiro [Δ⁵-pregnene-21-acetyloxy-17α-ol-11, 20-dione-3,2'-thiazolidine-4'-carboxylic acid]

15. The composition of claim 12, wherein said compound is:
Spiro [Δ⁵-pregnene-21-(N,N-dimethylglycyl)-oxy-17α-ol-11, 20-dione-3,2'-thiazolidine-4'-carboxylic acid]

16. The composition of claim 12, wherein said compound is: Spiro [Δ⁵-pregnene-17α, 21-diol-11, 20-dione-3,2'-thiazolidine-4'-carboxylic acid ethyl ester]

17. The composition of claim 12, wherein said compound is:
Spiro [Δ⁵-pregnene-21-(N,N-dimethylglycyl)-oxy-17α-ol-11, 20-dione-3,2'-thiazolidine-4'-carboxylic acid ethyl ester]

18. The composition of claim 12, wherein said compound is:
Spiro [Δ¹,⁴-pregnadiene-11β, 17α, 21-triol-20-one-3,2'-thiazolidine-4'-carboxylic acid]

19. The composition of claim 12, wherein said compound is:
Spiro [Δ¹,⁴-pregnadiene-21-acetyloxy-11β, 17α-diol-20-one-3,2'-thiazolidine-4'-carboxylic acid]

20. The composition of claim 12, wherein said compound is:
Spiro [Δ¹,⁴-pregnadiene-21-(N,N-dimethylglycyl)-oxy-11β, 17α-diol-20-one-3,2'-thiazolidine-4'-carboxylic acid]

21. The composition of claim 12, wherein said compound is:
Spiro [Δ¹,⁴-pregnadiene-21-(N,N-dimethylglycyl)-oxy-11β, 17α-diol-20-one-3,2'-thiazolidine-4'-carboxylic acid ethyl ester]

22. The composition of claim 12, wherein said compound is:
Spiro [Δ⁵-pregnene-17α, 21-isopropylidenedioxy-11β-ol-20-one-3,2'-thiazolidine-4'-carboxylic acid]

23. A method for alleviating inflammation in or on a warm-blooded animal exhibiting an inflammatory response which comprises administering thereto, an anti-inflammatory effective amount of a pro-drug compound of the formula:

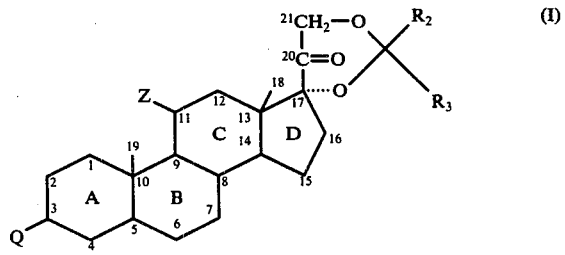

wherein Z respresents a member selected from the group consisting of =O, β—OH and β—O—R₁, wherein R₁ represents

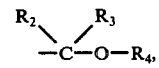

wherein R₄ represents a member selected from the group consisting of H and straight or branched $C_1$-$C_4$ alkyl, and wherein R₂ and R₃ which may be the same or different, represent a member selected from the group consisting of H, straight or branched $C_1$-$C_8$ alkyl, substituted $C_1$-$C_8$ alkyl, wherein at least one of the hydrogen atoms therein is substituted by a member selected from the group consisting of —N(R₄)₂, —CON(R₄)₂, a halogen atom, —COOR₄, —COOCH₂N(R₄)₂ and —COOCH₂—S—R₄, wherein R₄ is defined as above, and wherein R₂ and R₃ further represent a member selected from the group consisting of

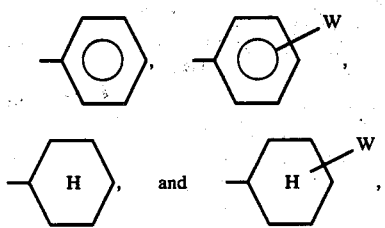

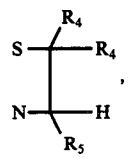

wherein W represents a member selected from the group consisting of —N(R$_{42}$, —CON(R$_4$)$_2$, a halogen atom, —COOR$_4$, —COOCH$_2$N(R$_4$)$_2$ and —COOCH$_2$—S—R$_4$, wherein R$_4$ is defined as above, with the proviso that R$_2$ and R$_3$ cannot simultaneously be H or wherein R$_2$ and R$_3$ taken together further represent a member selected from the group consisting of cyclic alkyl [—(CH$_2$)$_n$—] and cyclic heteroalkyl, wherein one of the carbon atoms is substituted by a member selected from the group consisting of N—R$_4$, N—COR$_4$ and —CO, wherein n is an integer of 5 to 7 and wherein R$_4$ is defined as above; wherein O represents

wherein R$_4$ is defined as above, and R$_5$ represents H, COOR$_4$ and —CON(R$_4$)$_2$, wherein R$_4$ is defined as above, provided the C$_4$-C$_5$ double bond in formula (I) is subject to migration to the C$_5$-C$_6$ position; and wherein with respect to ring (A) formula (I), the bond between C$_1$ and C$_2$ can be a single or double bond.

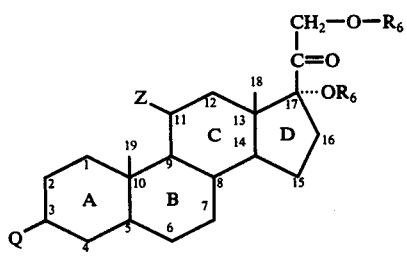
(II)

wherein Z represents a member selected from the group consisting of =O and β—OH; wherein R$_6$ represents a member selected from the group consisting of H and

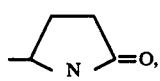

with the proviso that one of said R$_6$ is H, wherein R$_7$ represents a member selected from the group consisting of a C$_1$-C$_{12}$ straight, branched or cycloalkyl, a C$_1$-C$_{12}$ straight, branched or cycloalkenyl, a substituted C$_1$-C$_{12}$ straight, branched or cycloalkyl or alkenyl, —(CH$_2$)$_n$—CON(R$_2$)$_2$, wherein n is an integer of 1 to 6, a 2, 3 or 4 pyridyl, wherein at least one of the hydrogen atoms therein can be substituted by a member selected from the group consisting of —N(R$_4$)$_2$, —CON(R$_4$)$_2$, —SOR$_4$, a halogen atom, —COOR$_4$, —COOCH$_2$N(R$_4$)$_2$ and —COOCH$_2$—S—R$_4$, wherein R$_4$ is defined above,

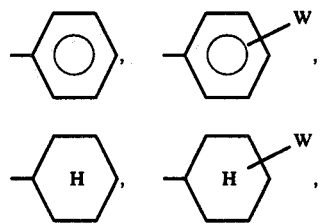

wherein W is defined above; wherein Q represents

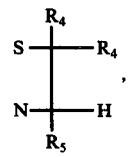

wherein R$_4$ is defined as above and R$_5$ represents a member selected from the group consisting of H, COOR$_4$ and —CON(R$_4$)$_2$; wherein R$_4$ is defined as above; wherein the bond between C$_1$ and C$_2$ in ring "A" of formula (II) can be a single or a double bond; and wherein, with respect to ring "A" in formula (II), the double bond between C$_4$ and C$_5$ is subject to migration to the C$_5$-C$_6$ position.

24. The method of claim 23, wherein said compound is:

Spiro [Δ$^5$-pregnene-17α, 21-diol-11, 20-dione-3,2'-thiazolidine-4'-carboxylic acid]

25. The method of claim 23, wherein said compound is:

Spiro [Δ$^5$-pregnene-21-acetyloxy-17α-ol-11, 20-dione-3,2'-thiazolidine-4'-carboxylic acid]

26. The method of claim 23, wherein said compound is:

Spiro [Δ$^5$-pregnene-21-(N,N-dimethylglycyl)-oxy-17α-ol-11, 20-dione-3,2'-thiazolidine-4'-carboxylic acid]

27. The method of claim 23, wherein said compound is:

Spiro [Δ$^5$-pregnene-17α, 21-diol-11, 20-dione-3,2'-thiazolidine-4'-carboxylic acid ethyl ester]

28. The method of claim 23, wherein said compound is:

Spiro [Δ$^5$-pregnene-21-(N,N-dimethylglycyl)-oxy-17α-ol-11, 20-dione-3,2'-thiazolidine-4'-carboxylic acid ethyl ester]

29. The method of claim 23, wherein said compound is:

Spiro [Δ$^{1,4}$-pregnadiene-11β, 17α, 21-triol-20-one-3,2'-thiazolidine-4'-carboxylic acid]

30. The method of claim 23, wherein said compound is:

Spiro [Δ$^{1,4}$-pregnadiene-21-acetyloxy-11β, 17α-diol-20-one-3,2'-thiazolidine-4'-carboxylic acid]

31. The method of claim 23, wherein said compound is: Spiro Δ$^{1,4}$-pregnadiene-21-(N,N-dimethylglycyl)-oxy-11β, 17α-diol-20-one-3,2'-thiazolidine-4'-carboxylic acid]

32. The method of claim 23, wherein said compound is: Spiro [Δ$^{1,4}$-pregnadiene-21-(N,N-dimethylglycyl)-oxy-11β, 17α-diol-20-one-3,2'-thiazolidine-4'-carboxylic acid ethyl ester]

33. The method of claim 23, wherein said compound is:
Spiro [Δ$^5$-pregnene-17α, 21-isopropylidenedioxy-11β-ol-20-one-3,2'-thiazolidine-4'-carboxylic acid]

34. The method of claim 23, wherein said compound is maintained in combination with a nontoxic pharmaceutically acceptable inert carrier material.

35. The method of claim 34, wherein said carrier material is an oral carrier material.

36. The method of claim 34, wherein said carrier material is a topical carrier material.

37. The method of claim 36, wherein said topical carrier material is triocetin.

* * * * *